United States Patent
McKay

(10) Patent No.: US 9,554,831 B2
(45) Date of Patent: Jan. 31, 2017

(54) INTERVERTEBRAL SPINAL IMPLANT AND METHOD

(71) Applicant: Warsaw Orthopedic, Inc., Warsaw, IN (US)

(72) Inventor: William F. McKay, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 162 days.

(21) Appl. No.: 14/257,339

(22) Filed: Apr. 21, 2014

(65) Prior Publication Data

US 2015/0297269 A1 Oct. 22, 2015

(51) Int. Cl.
*A61B 17/70* (2006.01)

(52) U.S. Cl.
CPC ....... *A61B 17/7068* (2013.01); *A61B 17/7065* (2013.01); *A61B 17/7067* (2013.01)

(58) Field of Classification Search
CPC ............ A61B 17/7065; A61B 17/7067; A61B 17/7068
See application file for complete search history.

(56) References Cited

U.S. PATENT DOCUMENTS

| | | | | |
|---|---|---|---|---|
| 8,062,337 | B2* | 11/2011 | Bruneau | A61B 17/7065 606/249 |
| 8,236,031 | B2 | 8/2012 | Bucci | |
| 2004/0049190 | A1* | 3/2004 | Biedermann | A61B 17/7008 606/257 |
| 2005/0203624 | A1* | 9/2005 | Serhan | A61B 17/7062 623/17.11 |
| 2008/0228225 | A1 | 9/2008 | Trautwein et al. | |
| 2009/0048631 | A1* | 2/2009 | Bhatnagar | A61B 17/7004 606/246 |
| 2009/0254122 | A1 | 10/2009 | Khalife | |
| 2010/0106190 | A1* | 4/2010 | Linares | A61B 17/7065 606/249 |
| 2011/0218572 | A1 | 9/2011 | Lechmann et al. | |
| 2012/0215262 | A1 | 8/2012 | Culbert et al. | |
| 2013/0282128 | A1* | 10/2013 | McKay | A61F 2/4465 623/18.11 |

* cited by examiner

*Primary Examiner* — Ellen C Hammond

(57) ABSTRACT

A spinal implant is provided. The spinal implant includes a body extending between a proximal end and a distal end. The proximal end defines a notch configured for disposal of a first vertebra. The distal end includes a protrusion configured for disposal in a second vertebra. The proximal and distal ends are movable relative to one another between an unexpanded position in which the spinal implant is inserted between lamina and an expanded position in which the spinal implant is disposed between the lamina.

14 Claims, 4 Drawing Sheets

INTERVERTEBRAL SPINAL IMPLANT AND METHOD

BACKGROUND

The rapid and effective repair of bone defects caused by injury, disease, wounds, or surgery is a goal of orthopedic surgery. Toward this end, a number of bone implants have been used or proposed for use in the repair of bone defects including spinal stenosis. The biological, physical, and mechanical properties of the bone implants are among the major factors influencing their suitability and performance in various orthopedic applications.

Spinal stenosis is a narrowing of the spinal canal, which can lead to an impingement on the spinal cord and various nerves resulting in symptoms of moderate to extreme pain. Bone implants are used to alleviate symptoms associated with spinal stenosis. Bone implants are also used to repair bone that has been damaged by disease, trauma, or surgery. In some types of spinal fusion, for example, bone implants are used to replace the cushioning disc material between the vertebrae or to repair a degenerative facet joint.

During certain spinal corrective procedures, such as for example, alleviating spinal stenosis pain and/or a spinal fusion procedure, bone implants are positioned in an interspinous process space. The interspinous process bone implants attempt to lessen pain caused by spinal stenosis by redirecting pressure away from the foramina. Interspinous process bone implants can also be used to facilitate bone remodeling and new bone growth, and integration of the bone implant (e.g., allograft) into host bone. However, interspinous process implants carry several inherent drawbacks. Exemplary disadvantages of interspinous process bone implants include difficulty mechanically fixing the implant to the spinous processes; erosion of adjacent bone; and fracture of the spinous process due to the relatively thin and weak nature of the spinous processes.

The present disclosure offers several advantages over interspinous process implants to lessen pain caused by spinal stenosis and/or maintain an intervertebral space during fusion of adjacent vertebrae.

SUMMARY

The present disclosure includes a spinal implant configured for engagement with lamina bone, which is much closer to a neutral axis of the spine and has greater strength and rigidity than spinous processes. The spinal implant is expandable to a selected length to apply a distracting force on the lamina to reduce the amount of soft tissue that protrudes into the spinal canal and foramen, which can be a cause of the pain associated with spinal stenosis.

In some embodiments, the spinal implant of the present disclosure allows load to be transferred away from the spinous process to the intervertebral foramen and/or lamina. This reduces the risk of fracture of the spinous process, and bone resorption problems resulting from spinous process fracture.

In one embodiment, there is a spinal implant, comprising: a body extending between a proximal end and a distal end, the proximal end defining a notch or protrusion configured for disposal in a first vertebra, the distal end comprising a protrusion or protrusion configured for disposal in a second vertebra, wherein the proximal and distal ends of the body are movable relative to one another between an unexpanded position in which the spinal implant is configured to be inserted between lamina and an expanded position in which the spinal implant is configured to be disposed between the lamina.

In one embodiment, in accordance with the principles of the present disclosure, a spinal implant is provided. The spinal implant includes a body extending between a proximal end and a distal end. The proximal end defines a notch configured for disposal of a first vertebra. The distal end includes a protrusion configured for disposal in a second vertebra. The proximal and distal ends are movable relative to one another between an unexpanded position in which the spinal implant is inserted between lamina and an expanded position in which the spinal implant is disposed between the lamina.

In one embodiment, a spinal implant is provided. The spinal implant includes a body extending between a proximal end and a distal end. The proximal end defines a notch configured for disposal of a first vertebra. The distal end includes a protrusion configured for disposal in a second vertebra. The body includes a jacking member configured for engagement with a driver. The proximal and distal ends are movable relative to one another via the jacking member between an unexpanded position in which the spinal implant is inserted between lamina and an expanded position in which the spinal implant is disposed between the lamina.

In one embodiment, a method for treating a spine disorder is provided. The method includes providing a spinal implant comprising a body extending between a proximal end and a distal end. The proximal end defines a notch configured for disposal of a first vertebra. The distal end includes a protrusion configured for disposal in a second vertebra. The proximal and distal ends are movable relative to one another between an unexpanded position and an expanded position. A cavity is formed in the second vertebra. The protrusion is disposed in the cavity. The body is rotated relative to the second vertebra to position the first vertebra in the notch.

In one embodiment, there is a spinal implant, comprising: a body extending between a proximal end and a distal end, the proximal end configured for disposal in a first vertebra, the distal end configured for disposal in a second vertebra, wherein the proximal and distal ends are movable relative to one another between an unexpanded position in which the spinal implant is configured to be inserted between lamina and an expanded position in which the spinal implant is configured to be disposed between the lamina so as to allow elasticity during motion.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE FIGURES

In part, other aspects, features, benefits and advantages of the embodiments will be apparent with regard to the following description, appended claims and accompanying drawings where:

Figure 1:
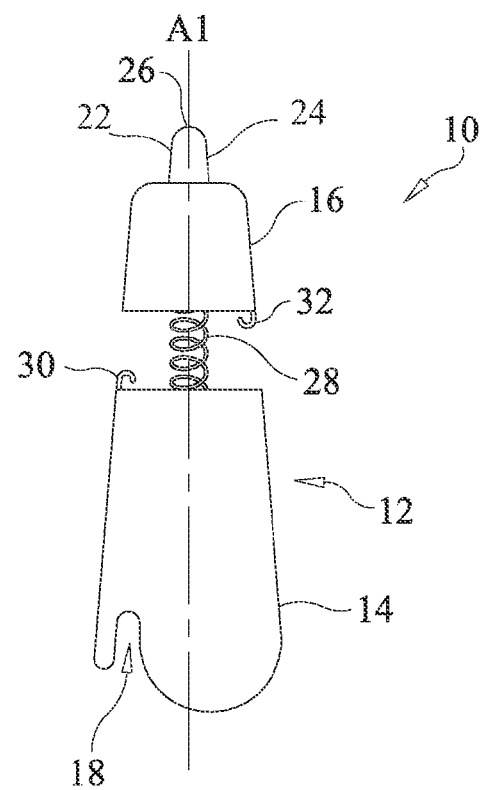
FIG. 1 illustrates a perspective view of one embodiment of a spinal implant in accordance with the principles of the present disclosure.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

It is noted that, as used in this specification and the appended claims, the singular forms "a," "an," and "the," include plural referents unless expressly and unequivocally limited to one referent. Thus, for example, reference to "a spinal implant" includes one, two, three or more spinal implants.

Reference will now be made in detail to certain embodiments of the present disclosure, examples of which are illustrated in the accompanying drawings. While the present disclosure will be described in conjunction with the illustrated embodiments, it will be understood that they are not intended to limit the disclosure to those embodiments. On the contrary, the present disclosure is intended to cover all alternatives, modifications, and equivalents, which may be included within the invention as defined by the appended claims.

The headings below are not meant to limit the disclosure in any way; embodiments under any one heading may be used in conjunction with embodiments under any other heading.

In one embodiment, a system for correcting a spinal abnormality, such as, for example, spinal stenosis, is provided. The system includes an interlaminar distraction implant. In one embodiment, the implant includes an elastomeric or spring loaded member for lengthening the implant. In one embodiment, the implant includes an internal mechanical mechanism that lengthens the implant via a pre-tension mechanism. In one embodiment, the implant includes an expanding mechanism. In one embodiment, the implant is flexible. In one embodiment, the implant has a rigid structure.

In some embodiments, the spinal implant of the present disclosure allows load to be transferred away from the spinous process to the intervertebral foramen and/or lamina. This reduces the risk of fracture of the spinous process, and bone resorption problems resulting from spinous process fracture.

In one embodiment, the implant is inserted in a minimally invasively procedure. In some embodiments, the implant reduces spinal stenosis pain. The implant can be directly anchored into lamina bone and closer to a neutral axis of a spine. In some embodiments, the implant is distracted to a selected length while being anchored between lamina to reduce the amount of soft tissue that protrudes into a spinal canal and foramen, which is a cause of pain associated with spinal stenosis.

In one embodiment, a method of employing the disclosed spinal implant is provided. The implant is inserted between lamina in the interlaminar space. In one embodiment, the method includes inserting an elongated member such as a guidewire, rod, or pin such as, for example, a Steinmann pin into a superior lamina. In one embodiment, the Steinmann pin is inserted using fluoroscopic imaging. A small hole is drilled or reamed into the superior lamina, which is sized and dimensioned to receive a docking tip of the implant. The implant is guided along the Steinmann pin such that the docking tip is disposed in the hole. In one embodiment, an instrument, such as, for example, a gauge instrument is inserted through the skin of a patient directly above the implant into engagement with a port of the implant. The gauge instrument is manipulated to move the implant into a position between adjacent lamina. The gauge instrument is rotated within the port to actuate the internal mechanical mechanism, axially spacing the implant and anchoring the implant between the lamina. The axial displacement of the implant applies a distracting force on the lamina to reduce soft tissue stenosis in the spinal canal and foramen.

Spinal Implant

Referring to FIGS. 1-6, FIG. 1 illustrates a perspective view of an embodiment of a spinal implant, such as, for example, a spacer 10 is illustrated. In this illustrated embodiment, spacer 10 comprises a body 12 configured for maintaining a space between vertebral tissue, such as, for example, adjacent lamina of a vertebrae V (in FIG. 4). Body 12 has a bullet-shaped configuration. In some embodiments, body 12 is variously configured, such as, for example, round, oval, oblong, square, triangular, rectangular, irregular, uniform, non-uniform, consistent, and/or variable.

Body 12 extends between a proximal end 14 and a distal end 16 defining a longitudinal axis A1 therebetween. Body 12 tapers from proximal end 14 to distal end 16. In some embodiments, body 12 has a uniform width along its length, which is defined between ends 14, 16. Body 12 is cannulated along its length such that an elongated element 20, such as, for example, a Steinmann pin or guidewire can be positioned therein.

Proximal end 14 includes an inner surface defining a notch 18 configured for disposal of a first vertebra, such as, for example, an inferior lamina L1. Notch 18 has a V-shaped configuration. In some embodiments, notch 18 is variously configured, such as, for example, U-shaped, parabolic-shaped, oval, oblong, triangular, arcuate, square, polygonal, irregular, uniform, non-uniform, offset, staggered, undulating, arcuate, variable and/or tapered. In some embodiments, the notch can be instead a projection (not shown).

Distal end 16 includes a protrusion, such as, for example, a tapered element 22 configured for disposal in a second vertebra, such as, for example, a superior lamina L2, adjacent inferior lamina L1. Tapered element 22 includes a roughened outer surface that adheres to tissue, such as, for example, bone tissue. In some embodiments, the outer surface has alternate configurations, such as, for example, planar, undulating, porous, semi-porous, dimpled, polished and/or textured. Tapered element 22 extends between a proximal end 24 and a distal tip 26 defining a cone-shaped configuration therebetween. Proximal end 24 has a diameter substantially equal to one-half of a diameter of proximal end 14 of body 12. Distal tip 26 has a rounded configuration. In one embodiment, distal tip 26 is pointed for penetrating engagement with tissue, such as, for example, spinal tissue. In some embodiments, the protrusion can be instead a recess (not shown).

Proximal and distal ends 14, 16 are movable, such as, for example, axially translatable, relative to one another between an unexpanded position and an expanded position. In the unexpanded position, body 12 can be inserted between lamina L1, L2. Upon placement of body 12 between lamina L1, L2, ends 14, 16 are axially spaced to the expanded position to apply a tensile force on lamina L1, L2, lessening impingement on nerves and the spinal cord by the foramen and the spinal canal. Body 12 includes an expandable intermediate portion 28 disposed between ends 14, 16. Intermediate portion 28 includes a biasing member, such as, for example, a spring. Spring resiliently biases body 12 to the expanded position.

Proximal end 14 includes a mating part, such as, for example, a female mating part 30. Distal end 16 includes a mating part, such as, for example, a male mating part 32. Mating parts 30, 32 are detachably engagable with one another in the unexpanded position such that proximal and distal ends 14, 16 are in a provisionally locked orientation relative to one another in the unexpanded position. To move body 12 to the expanded position, ends 14, 16 are relatively rotated to disengage mating parts 30, 32 such that intermediate portion 28 axially spaces ends 14, 16 from one another. In one embodiment, mating parts 30, 32 include hook elements. In some embodiments, mating parts 30, 32 include alternative configurations, such as, for example, nails, serrated, textured, staggered, uneven, undulating, smooth, barbs and/or raised elements to facilitate detachable engagement with one another.

Body 12 comprises at least one of stainless steel alloys, commercially pure titanium, titanium alloys, Grade 5 titanium, cobalt-chrome alloys, stainless steel alloys, calcium phosphate, polyaryletherketone (PAEK), polyetheretherketone (PEEK), polyetherketoneketone (PEKK), polyetherketone (PEK), carbon-PEEK composites and PEEK-BaSO4.

Body 12 may be made from materials, such as for example, polyurethane, polyurea, polyether(amide), PEBA, thermoplastic elastomeric olefin, copolyester, and styrenic thermoplastic elastomer, metal alloys with high non-ferrous metal content and a low relative proportion of iron, carbon fiber, glass fiber, plastics, ceramics or combinations thereof.

In various embodiments, some or all of body 12 may comprise material that is bioresorbable. Examples of suitable biodegradable and/or bioresorbable material include, but is not limited to, poly (alpha-hydroxy acids), poly (lactide-co-glycolide) (PLGA), polylactide (PLA), polyglycolide (PG), polyethylene glycol (PEG), conjugates of poly (alpha-hydroxy acids), polyorthoesters, polyaspirins, polyphosphagenes, collagen, starch, chitosans, gelatin, alginates, dextrans, vinylpyrrolidone, polyvinyl alcohol (PVA), PVA-g-PLGA, PEGT-PBT copolymer (polyactive), methacrylates, poly (N-isopropylacrylamide), PEO-PPO-PEO (pluronics), PEO-PPO-PAA copolymers, PLGA-PEO-PLGA, or combinations thereof. In some embodiments, some or all of body 12 may comprise material that is shape memory material. Examples of suitable shape memory materials include, but are not limited to shape memory alloys such as nickel-titanium alloys (e.g., nitinol), copper-aluminum-nickel, copper-zinc-aluminum, and iron-manganese-silicon alloys and shape memory polymers such as polyurethanes, polyurethanes with ionic or mesogenic components, block copolymers comprising polyethyleneterephthalate and polyethyleneoxide, block copolymers containing polystyrene and polybutadiene, polyesterurethanes with methylenebis and butanediol, epoxy resins.

In one embodiment, tapered element 22 is movable relative to distal end 16 of body 12 between an unexpanded configuration and an expanded configuration. In the unexpanded configuration, distal tip 26 protrudes from distal end 16 and proximal end 24 remains disposed within distal end 16 of body 12 such that body 12 is insertable between vertebrae. With spacer 10 disposed between lamina L1, L2, body is moved to the expanded configuration, in which proximal end 24 and distal tip 26 of tapered element 22 protrude from distal end 16 of body 12. In the expanded configuration, body 12 applies a tensile force on lamina L1, L2.

Figure 2:
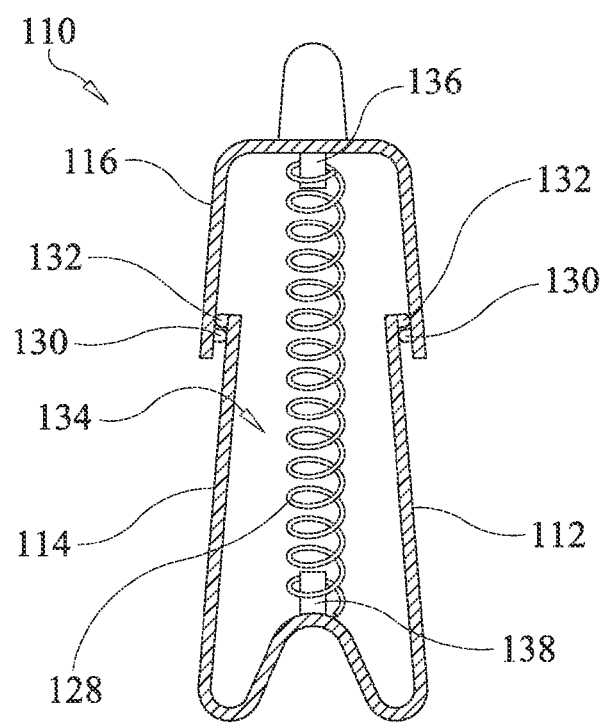
FIG. 2 illustrates a top view, in cross section, of an embodiment of the spinal implant shown in FIG. 1.

In one embodiment, as shown in FIG. 2, illustrated is a spinal implant, such as, for example, a spacer 110, similar to spacer 10 described with regard to FIG. 1. Spacer 110 includes a body 112, similar to body 12 described herein, extending between a proximal end 114 and a distal end 116. As illustrated, proximal end 114 is disposed within distal end 116. In some embodiments, distal end 116 is disposed within proximal end 114. Distal end 116 includes a protrusion, such as, for example, a tapered element 122, similar to tapered element 22 described herein. Body 112 includes an intermediate portion, such as, for example, a spring 128 disposed within a cavity 134 defined in ends 114, 116. Spring 128 is engaged to a post 136 extending from distal end 116 and a post 138 extending from proximal end 14 to limit the axial displacement of ends 114, 116 relative to one another in the expanded configuration. Spring 128 resiliently biases ends 114, 116 in opposing directions. Ends 114, 116 each include mating parts 130, 132, similar to mating parts 30, 32 described herein, that extend into cavity 134 to resist the axial displacement of ends 114, 116 relative to one another in the unexpanded configuration. To move from the unexpanded configuration to the expanded configuration, ends 114, 116 are relatively rotated to disengage mating parts 130, 132 such that spring 128 axially spaces ends 114, 116 and expands cavity 134.

Figure 2A:
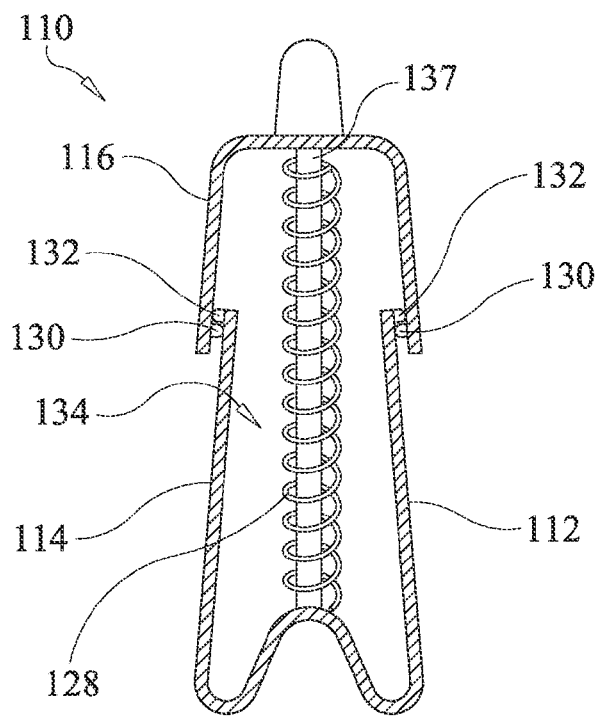
FIG. 2A illustrates a top view, in cross section, of an embodiment of the spinal implant shown in FIG. 1.

In one embodiment, as shown in FIG. 2A, illustrated is spacer 110. Spring 128 is engaged to a post 137 extending from distal end 116 to proximal end 114. Post 137 is a central solid post that spring 128 is configured to wrap around. Alternatively, in one embodiment, spring 128 is disposed within a hollow cylinder which provides rigidity to spacer 110. The post 137 transversely extends from the distal end 116 to the proximal end 114 and provides more rigidity, and elasticity as compared to FIG. 2. A spinal implant that is completely rigid will cause unwanted erosion. Therefore, this spinal implant prevents or reduces such unwanted erosion by providing rigidity as well as longitudinal elasticity.

The spinal implants provided allow for inter-laminar distraction to decompress nerves causing pain (e.g., disc herniation/bulging, hypertrophic ligaments and/or facets, stenosis, facet degeneration/slippage, etc.). The spinal implants provided, in some embodiments, are implanted in the midline of the posterior spinal column.

Figure 3:
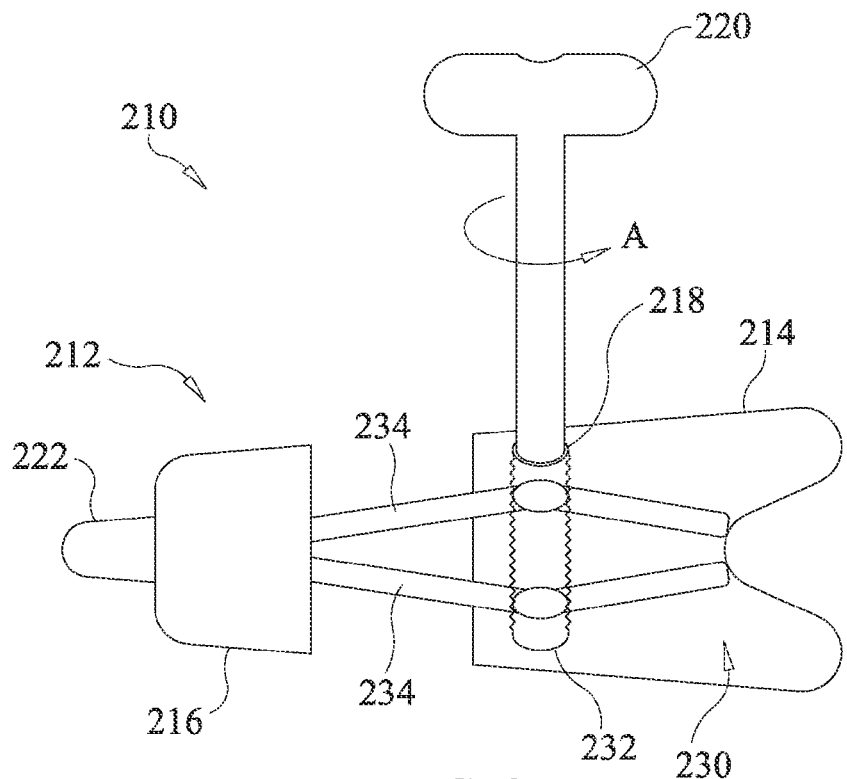
FIG. 3 illustrates a perspective view, in part cross section, of an embodiment of the spinal implant shown in FIG. 1.

Referring to FIG. 3, illustrated is a top view, in part cross section, of an embodiment of a spinal implant, such as, for example, a spacer 210, similar to spacer 10 disclosed with regard to FIG. 1. In this illustrated embodiment, spacer 210 includes a body 212, similar to body 12 described herein, including a proximal end 214 and a distal end 216. Distal end 216 includes a tapered element 222, similar to tapered element 22 described herein. Proximal end 214 includes a bore 218 configured for disposal of a driver, such as, for example, an implantation tool 220.

Implantation tool 220 includes, but is not limited to, a driver, wrench, spanner, screwdriver, or other turning tool, and the like that can engage body 212. The implantation tool 220 may be used manually (e.g., turnable by hand) or by an automatic device (e.g., using a drill, power driver, etc.). The implantable tool 220 may be made from materials, such as for example, polyurethane, polyurea, polyether(amide), PEBA, thermoplastic elastomeric olefin, copolyester, and styrenic thermoplastic elastomer, steel, aluminum, stainless steel, titanium, metal alloys with high non-ferrous metal content and a low relative proportion of iron, carbon fiber, glass fiber, plastics, ceramics or combinations thereof. In various embodiments, the implantation tool 220 is not biodegradable.

Body 212 includes a jacking member 230 configured for engagement with implantation tool 220. Proximal and distal ends 214, 216 are movable relative to one another via jacking member 230 between the unexpanded position and the expanded position. Jacking member 230 includes a screw 232 disposed in coaxial alignment with bore 218. Screw 232 includes a head configured for mating engagement with a distal end of implantation tool 220 to rotate screw 232 within bore 218. Jacking member 230 includes a pair of hinges 234 connected with proximal end 214 and distal end 216 of body 212. Screw 232 is threadedly engaged to a pivot point of hinges 234 such that the rotation of screw 232 causes hinges 234 to flex outwardly or inwardly to drive the relative axial movement of ends 214, 216. In some embodiments, jacking member 230 is variously configured, such as, for example, as a bell crank, cam, connection rod, crank arm, jack, radius bar, winch, a series of gears or a yoke.

Figure 3A:
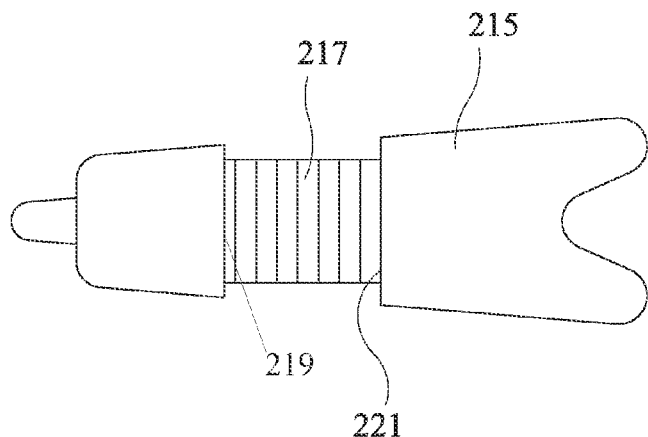
FIG. 3A illustrates a perspective view, of an embodiment of the spinal implant shown in FIG. 1.

In one embodiment, referring to FIG. 3A, illustrated is a side view of a screw member 217 of implant body 212, similar to jacking member 230 disclosed with regard to FIG. 3. The proximal end 219 and distal end 215 of the implant body are connected by a screw member 217, where rotation of the proximal end 219 and/or distal end 215 of the implant body will allow the proximal and distal end of the implant body to move closer together if turned in one direction, or move further apart if rotated in an opposite direction. In this way, the length of the implant body can be adjusted by the rotation. Screw member 217 includes a proximal end and a distal end with an intermediate portion comprising a screw thread 221 that engages reciprocating internal screw threading (not shown) in the proximal and/or distal end.

Figure 4:
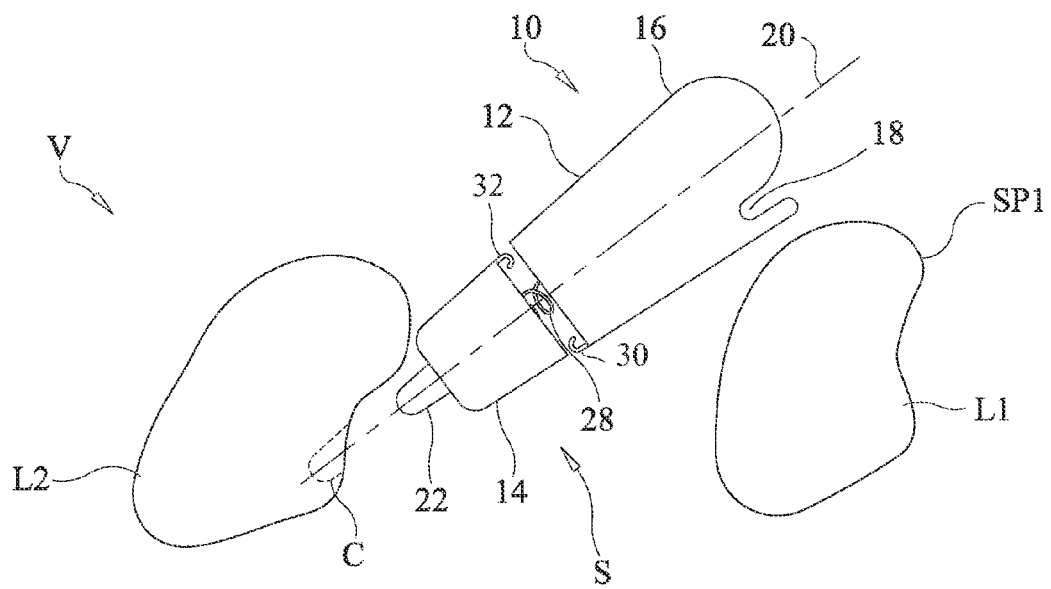
FIG. 4 illustrates a perspective view of the spinal implant shown in FIG. 1 being inserted between vertebrae using a guidewire.
Figure 5:
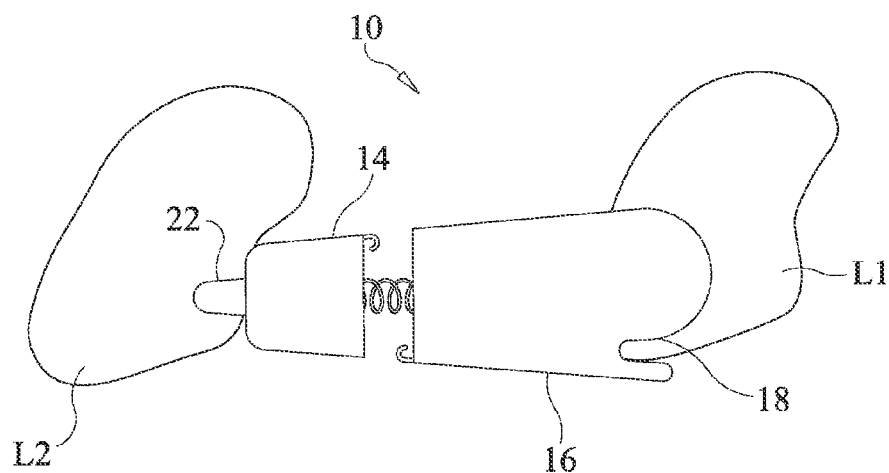
FIG. 5 illustrates a side view of an embodiment of the spinal implant shown in FIG. 1 disposed between vertebrae.

FIGS. 4 and 5 illustrate a method for treating a spine disorder, such as, for example, spinal stenosis pain. A medical practitioner obtains access to a surgical site including vertebrae V in any appropriate manner, such as through incision and retraction of tissues. In some embodiments, spacer 10 can be used in any existing surgical method or technique including open surgery, mini-open surgery, minimally invasive surgery and percutaneous surgical implantation, whereby vertebrae V is accessed through a mini-incision, or sleeve that provides a protected passageway to the area. Once access to the surgical site is obtained, the particular surgical procedure can be performed for treating the spine disorder.

An incision is made in a body of a patient and a cutting instrument (not shown) creates a surgical pathway along, in some embodiments, a substantially posterior approach for implantation of components of spacer 10 within the patient body. Spacer 10 is oriented in the unexpanded position, as shown in FIG. 4, with mating parts 28, 30 in engagement. Guidewire 20 is inserted into lamina L2. A drill (not shown) is guided along guidewire 20 into contact with lamina L2 and actuated to form a cavity C in lamina L2 sized and dimensioned for disposal of tapered element 22 while allowing for some rotational movement within cavity C. The drill is removed from the surgical site and spacer 10 is positioned over guidewire 20 and axially guided along guidewire 20 toward lamina L2 to dispose tapered element 22 in cavity C. Guidewire 20 is removed from the surgical site. Spacer 10 is rotated relative to lamina L2 about tapered element 22 guiding notch 18 along a spinous process SP1. Spacer 10 is rotated until lamina L1 is disposed in notch 18 such that ends 14, 16 are disposed in an interlaminar space S between lamina L1, L2. Ends 14, 16 are relatively rotated to disengage mating parts 30, 32 such that intermediate portion 28 axially spaces ends 14, 16 and anchors distal end 16 with lamina L2 and proximal end 14 with lamina L1 to alleviate pressure on nerves and the spinal cord. The spinal implant device provided allows notch 18 to engage the lamina L1 and the lamina L1 is seated just above notch 18 as shown in FIG. 5.

Figure 6:
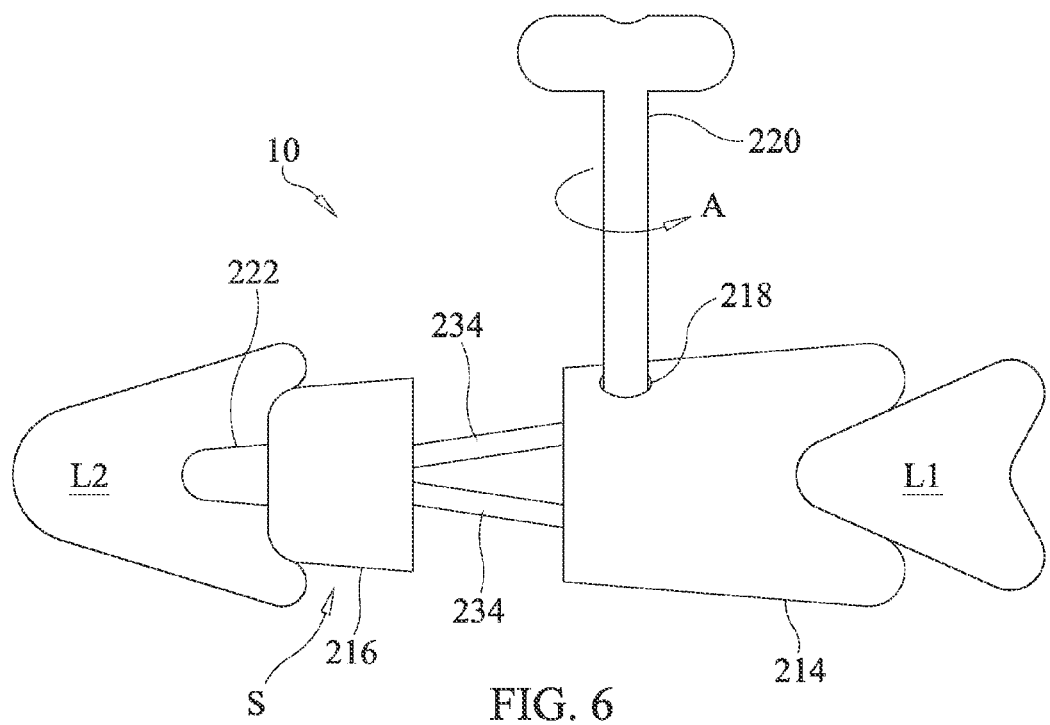
FIG. 6 illustrates a cross sectional view of an embodiment of the spinal implant shown in FIG. 1, disposed between vertebrae and with an implantation tool.

FIG. 6 illustrates a method for treating a spine disorder, such as, for example, spinal stenosis pain, similar to the method described with regard to FIGS. 4 and 5. In this embodiment, spacer 210 is disposed between lamina L1, L2 in the interlaminar space S. With body 212 located between lamina L1, L2, implantation tool 220 is inserted within bore 218 into engagement with screw 232 and rotated, in the direction shown by arrow A in FIG. 6, flexing hinges 234 inwardly. The inward flexion of hinges 234 axially spaces ends 214, 216 and anchors proximal end 214 with lamina L1 and distal end 216 with lamina L2. In some embodiments, implantation tool 220 is used to wedge spacer 20 between lamina L1, L2.

Radiographic markers can be included on spacer 10 to permit the user to accurately position spacer 10 into the desired site of the patient. These radiographic markers will also permit the user to track movement of spacer 10 at the site over time. In this embodiment, the user may accurately position spacer 10 in the site using any of the numerous diagnostic imaging procedures. Such diagnostic imaging procedures include, for example, X-ray imaging or fluoroscopy. Examples of such radiographic markers include, but are not limited to, barium, calcium phosphate, and/or metal beads. For example, the radiographic marker can be ring-shaped or dispersed as small pellets throughout spacer 10.

In various embodiments, spacer 10 may include a transparent or translucent portion that can be visualizable by ultrasound, fluoroscopy, x-ray, or other imaging techniques. In such embodiments, the transparent or translucent portion may include a radiopaque material or ultrasound responsive topography that increases the contrast of spacer 10 relative to the absence of the material or topography.

Therapeutic Agents

In various embodiments, spacer 10 comprises a drug depot attached or coated thereto. A drug depot comprises a physical structure to facilitate implantation and retention in a desired site (e.g., a disc space, a spinal canal, a tissue of the patient, etc.) or adjacent to the desired site. The drug depot also comprises the drug. The term "drug" as used herein is generally meant to refer to any substance that alters the physiology of a patient. The term "drug" may be used interchangeably herein with the terms "therapeutic agent", "therapeutically effective amount", and "active pharmaceutical ingredient". It will be understood that a "drug" formulation may include more than one therapeutic agent, wherein exemplary combinations of therapeutic agents include a combination of two or more drugs. The drug provides a concentration gradient of the therapeutic agent for delivery to the site. In various embodiments, the drug depot provides an optimal drug concentration gradient of the therapeutic agent at a distance of up to about 1 cm to about 5 cm from the implant site.

Examples of drugs suitable for use in the drug depot, include, but are not limited to an anti-inflammatory agent, analgesic agent, or osteoinductive growth factor or a combination thereof. Anti-inflammatory agents include, but are not limited to, salicylates, diflunisal, indomethacin, ibuprofen, naproxen, tolmetin, ketorolac, diclofenac, ketoprofen, fenamates (mefenamic acid, meclofenamic acid), enolic acids (piroxicam, meloxicam), nabumetone, celecoxib, etodolac, nimesulide, apazone, gold, sulindac or tepoxalin; antioxidants, such as dithiocarbamate, and other compounds such as sulfasalazine[2-hydroxy-5-[-4-[C2-pyridinylamino) sulfonyl]azo]benzoic acid], steroids, such as fluocinolone, cortisol, cortisone, hydrocortisone, fludrocortisone, prednisone, prednisolone, methylprednisolone, triamcinolone, betamethasone, dexamethasone, beclomethasone, fluticasone or a combination thereof.

Suitable osteoinductive factors include, but are not limited to, a bone morphogenetic protein, a growth differentiation factor, a LIM mineralization protein or a combination thereof.

Suitable analgesic agents include, but are not limited to, acetaminophen, lidocaine, bupivicaine, opioid analgesics such as buprenorphine, butorphanol, dextromoramide, dezocine, dextropropoxyphene, diamorphine, fentanyl, alfentanil, sufentanil, hydrocodone, hydromorphone, ketobemidone, levomethadyl, mepiridine, methadone, morphine, nalbuphine, opium, oxycodone, papaveretum, pentazocine, pethidine, phenoperidine, piritramide, dextropropoxyphene, remifentanil, tilidine, tramadol, codeine, dihydrocodeine, meptazinol, dezocine, eptazocine, flupirtine or a combination thereof. Analgesics also include agents with analgesic properties, such as for example, amitriptyline, carbamazepine, gabapentin, pregabalin, clonidine, or a combination thereof.

A "depot" includes but is not limited to capsules, microspheres, particles, gels, coating, matrices, wafers, pellets or other pharmaceutical delivery compositions. A depot may comprise a biopolymer that is either biodegradable or non-degradable. A depot may comprise a biopolymer that may provide for immediate release or sustained release or controlled release. Examples of suitable sustained release biopolymers include but are not limited to poly (alpha-hydroxy acids), poly (lactide-co-glycolide) (PLGA), polylactide (PLA), polyglycolide (PG), polyethylene glycol (PEG) conjugates of poly (alpha-hydroxy acids), polyorthoesters, polyaspirins, polyphosphagenes, collagen, starch, chitosans, gelatin, alginates, dextrans, vinylpyrrolidone, polyvinyl alcohol (PVA), PVA-g-PLGA, PEGT-PBT copolymer (polyactive), methacrylates, poly (N-isopropylacrylamide), PEO-PPO-PEO (pluronics), PEO-PPO-PAA copolymers, PLGA-PEO-PLGA, or combinations thereof.

The drug depot may be any shape, for example, bullet shaped, spherical, substantially spherical, flaked, rod shaped, square, oval, etc. The drug depot comprises a body that is made from a biodegradable material. In alternative embodiments, the body may be made from a non-biodegradable material. A non-biodegradable body could be a porous hollow chamber filled with the therapeutic agent alone or incorporated into a degradable polymer. It may be desirable to make the body non-degradable to be able to retrieve it after it has released or exhausted its contents. Or the non-biodegradable body could be a small pump that pushes the contents out pores, port(s), or a cannula. The body of the drug depot may be solid and a therapeutic agent may be dispersed throughout the material that forms the body. The dispersal of the therapeutic agent may be even throughout the body or in various parts of the body in layers (e.g., one third, two thirds, three fourths, etc.).

As the biodegradable material of the body degrades within the tissue, the therapeutic agent is released. Suitable sustained release materials may be used in the drug depot to carry the one or more therapeutic agents and control the release of the therapeutic agent(s). For example, microspheres may be used to encapsulate the therapeutic agent; the therapeutic agent-containing microspheres are then dispersed through the body of the drug depot.

The drug depot can be designed for gradient variations in biodegradability to hold the depot in place while the secondary material releases its contents. The drug depot may have a width from about 1 mm to about 6 mm and a length from about 5 mm to about 20 mm. Selection of suitable lengths and widths for the drug depot will depend upon the targeted implant site; dosage required and is well within the abilities of those having ordinary skill in the art.

In various embodiments, procedures for making the drug depot include, but are not limited to, extrusion-spheroidization, for spherical depots where the active pharmaceutical ingredient (API) and any inactive ingredients (excipients, binders, etc.) are pre-mixed, then wetted with water, in a high shear mixer to form a damp mass. The damp mass is then transferred into an extruder where it is forced through a screen or die plate, where it forms an essentially solid, cylindrical extrudate of uniform shape and size. The size of the opening in the screen or die dictates the resultant drug depot size. The extrudate is fed onto a rotating disk, which may be smooth or may contain a grid (waffled, grooved, etc.) and the extrudate breaks into small cylinders, which in time are rounded into spherically shaped solids. Subsequently, the drug depots are dried to the desired residual moisture content, typically in a fluid bed dryer. Any oversized or undersized product is removed by sieving, and the resulting drug depots have a narrow size distribution.

In various embodiments, the API is layered on the solid body of the drug depot by solution or suspension layering or powder layering techniques. In solution or suspension layering, an API and any inactive ingredients (excipients, binders, etc.) are suspended or dissolved in water or an organic solvent. The resulting liquid is sprayed onto the outside of a body, which may include, for example, nonpareil sugar seed (sugar sphere), microcrystalline cellulose depots and the like, to make the depot having the desired potency. Solution or suspension layering may be conducted using a wide variety of process techniques, for example, by fluidized bed, Wurster bottom spray techniques, or the like. When the desired potency has been achieved, the depots are dried to the desired residual moisture content. Any oversized or undersized product may be removed by sieving, and the resulting depots are narrow in size distribution.

Powder layering may also be used to make the drug depot. Powder layering involves the application of a dry powder to the body material. The powder may contain the drug, or may include excipients such as a binder, flow aid, inert filler, and the like. In the powder layering technique a pharmaceutically acceptable liquid, which may be water, organic solvent, with or without a binder and/or excipients, is applied to the body material while applying the dry powder until the desired potency is achieved. When the desired potency has been achieved, the drug depots may be seal coated to improve their strength, and are then dried to the desired moisture content. Any oversized or undersized product is removed by sieving, and the resulting drug depots are narrow in size distribution.

In one embodiment, the drug depot is made using a body of biodegradable material, such as, for example, polyglactin, polylactone, polylactide, etc. The body is then coated with a thin layer of the API, such as an anti-inflammatory agent, analgesic agent, etc. by solution, suspension, or powdered layering until the desired potency is achieved.

In various embodiments, the drug depot can be different sizes, for example, from about 1 mm to 5 mm and have a diameter of from about 0.01 to about 2 mm. The layer or layers will each have a layer thickness of from about 0.005 to 1.0 mm, such as, for example, from 0.05 to 0.75 mm.

Spacer 10 and/or drug depot may be disposable and sterilizable. In various embodiments, one or more components of spacer 10 are sterilized by radiation in a terminal sterilization step in the final packaging. Terminal sterilization of a product provides greater assurance of sterility than from processes such as an aseptic process, which require individual product components to be sterilized separately and the final package assembled in a sterile environment.

Typically, in various embodiments, gamma radiation is used in the terminal sterilization step, which involves utilizing ionizing energy from gamma rays that penetrates deeply in spacer 10. Gamma rays are highly effective in killing microorganisms, they leave no residues nor have sufficient energy to impart radioactivity to spacer 10. Gamma rays can be employed when spacer 10 is in the package and gamma sterilization does not require high pressures or vacuum conditions, thus, package seals and other components are not stressed. In addition, gamma radiation eliminates the need for permeable packaging materials.

In various embodiments, electron beam (e-beam) radiation may be used to sterilize one or more components of spacer 10. E-beam radiation comprises a form of ionizing energy, which is generally characterized by low penetration and high-dose rates. E-beam irradiation is similar to gamma processing in that it alters various chemical and molecular bonds on contact, including the reproductive cells of microorganisms. Beams produced for e-beam sterilization are concentrated, highly-charged streams of electrons generated by the acceleration and conversion of electricity. E-beam sterilization may be used, for example, when the drug depot includes a gelatin capsule.

Other methods may also be used to sterilize one or more components of spacer 10, including, but not limited to, gas sterilization, such as, for example, with ethylene oxide or steam sterilization.

In various embodiments, a kit is provided which may include additional parts along with spacer 10 combined together. The kit may include body 12 in a first compartment. A second compartment may include the drug depot, and the implantation tool, guidewire, and any other instruments needed for the implant. A third compartment may include gloves, drapes, wound dressings and other procedural supplies for maintaining sterility during the implanting process, as well as an instruction booklet. A fourth compartment may include cannulas and/or needles. Each tool may be separately packaged in a plastic pouch that is radiation sterilized. A cover of the kit may include illustrations of the implanting procedure and a clear plastic cover may be placed over the compartments to maintain sterility.

Spacer 10 may be used to treat a disease or condition such as for example, rheumatoid arthritis, osteoarthritis, sciatica, carpal tunnel syndrome, lower back pain, lower extremity pain, upper extremity pain, cancer, tissue pain and pain associated with injury or repair of cervical, thoracic, and/or lumbar vertebrae or intervertebral discs, rotator cuff, articular joint, TMJ, tendons, ligaments, muscles, and the like.

In various embodiments, spacer 10 and the drug depot are used to treat pain, or other diseases or conditions of the patient. Pain includes acute pain and neuropathic pain associated with spinal stenosis. Acute pain refers to pain experienced when tissue is being damaged or is damaged (e.g., injury, infection, etc.). As contrasted to acute pain, neuropathic pain serves no beneficial purpose. Neuropathic pain results when pain associated with an injury or infection continues in an area once the injury or infection has resolved. Sciatica provides an example of pain that can transition from acute to neuropathic pain. Sciatica refers to pain associated with the sciatic nerve which runs from the lower part of the spinal cord (the lumbar region), down the back of the leg and to the foot. Sciatica generally begins with a herniated disc. The herniated disc itself leads to local immune system activation. The herniated disc also may damage the nerve root by pinching or compressing it, leading to additional immune system activation in the area.

In various embodiments, once spacer 10 is anchored at the implant site and the drug is released from the drug depot over a period of time (e.g., days, months, years, etc.) and exhausted, the user (e.g., surgeon, physician, nurse, etc.) may remove the exhausted drug depot from spacer 10 without removing spacer 10 itself.

For example, the user can clip or cut the suture line holding the drug depot and replace it with another new drug depot. In this way, accurate and precise implantation of the replacement drug depot with minimal physical and psychological trauma to the patient result. Now successful treatment plans can be continued by merely replacing exhausted drug depots with new drug depots position at one or more treatment sites. In various embodiments, the drug depot is removed without removing spacer 10.

Radiographic markers can be included on spacer 10 and/or drug depot to permit the user to accurately position the depot into the site of the patient. These radiographic markers will also permit the user to track movement and degradation of the depot at the site over time. In this embodiment, the user may accurately position the depot in the site using any of the numerous diagnostic imaging procedures. Such diagnostic imaging procedures include, for example, X-ray imaging or fluoroscopy. When a subsequent image is taken of the treatment site, the user now can look for the degraded or exhausted drug depot and remove it and replace it with a new drug depot having fresh drug at the same or different dosage by, for example, threading a new suture or wire having the drug depot disposed on it through the hole and tying it to spacer 10.

The dosage administered, to an individual as single or multiple doses will vary depending upon a variety of factors, including the agent's pharmacokinetic properties, patient conditions and characteristics (sex, age, body weight, health, size, etc.), extent of symptoms, concurrent treatments, frequency of treatment and the effect desired. These factors can readily be determined by those of ordinary skill in the art.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. A spinal implant, comprising: a body extending between a proximal end and a distal end, the body including an expandable intermediate portion disposed between the proximal end and the distal end, the body comprising a shape memory material, the proximal end defining a notch configured for disposal in a first vertebra, and comprising a first mating part, the distal end comprising a protrusion configured for disposal in a second vertebra, and a second mating part, wherein the proximal and distal ends are movable relative to one another between an unexpanded position in which the spinal implant is configured to be inserted between lamina and an expanded position in which the spinal implant is configured to be disposed between the lamina, and the first mating part is configured to engage the second mating part in the unexpanded position, and the spinal implant is configured to move in the expanded position when the proximal end and the distal end are rotated relatively to one another to disengage the first mating part with the second mating part.

2. A spinal implant as recited in claim 1, wherein the intermediate portion includes a biasing member, the biasing member resiliently biasing the body to the expanded position.

3. A spinal implant as recited in claim 1, wherein the protrusion includes a roughened outer surface.

4. A spinal implant as recited in claim 1, wherein the protrusion has a rounded distal tip.

5. A spinal implant as recited in claim 1, wherein the protrusion has a cone-shaped configuration.

6. A spinal implant as recited in claim 1, wherein the protrusion is movable relative to the distal end.

7. A spinal implant as recited in claim 1, wherein the protrusion has a pointed distal tip configured for penetrating engagement with spinal tissue.

8. A spinal implant as recited in claim 1, wherein the first vertebra includes an inferior lamina and the second vertebra includes a superior lamina.

9. A spinal implant as recited in claim 1, wherein the body further comprises at least one of stainless steel alloys, commercially pure titanium, titanium alloys, Grade 5 titanium, cobalt-chrome alloys, stainless steel alloys, calcium phosphate, polyaryletherketone (PAEK), polyetheretherketone (PEEK), polyetherketoneketone (PEKK), polyetherketone (PEK), carbon-PEEK composites and PEEK-BaSO4.

10. A spinal implant as recited in claim 1, wherein the body is cannulated along its length.

11. A spinal implant as recited in claim 1, wherein the shape memory material comprises shape memory polymers such as polyurethanes, polyurethanes with ionic or mesogenic components, block copolymers comprising polyethyleneterephthalate and polyethyleneoxide, block copolymers containing polystyrene and polybutadiene, polyesterurethanes with methylenebis and butanediol, and epoxy resins.

12. A spinal implant as recited in claim 1, wherein the spinal implant is bullet shaped.

13. A spinal implant as recited in claim 1, wherein each mating part includes a hook.

14. A spinal implant, comprising: a body extending between a proximal end and a distal end, the proximal end comprising a first mating part, and the proximal end is configured for disposal in a first vertebra, the distal end comprising a second mating part, and the distal end is configured for disposal in a second vertebra, wherein the proximal and distal ends are movable relative to one another between an unexpanded position in which the spinal implant is configured to be inserted between lamina and an expanded position in which the spinal implant is configured to be disposed between the lamina so as to allow elasticity during motion, and the first mating part is configured to engage the second mating part in the unexpanded position, and the spinal implant is configured to move in the expanded position when the proximal end and the distal end are rotated relatively to one another to disengage the first mating part with the second mating part, the spinal implant being bullet shaped, and the body comprising a shape memory material.

* * * * *

UNITED STATES PATENT AND TRADEMARK OFFICE
CERTIFICATE OF CORRECTION

| | | |
|---|---|---|
| PATENT NO. | : 9,554,831 B2 | Page 1 of 1 |
| APPLICATION NO. | : 14/257339 | |
| DATED | : January 31, 2017 | |
| INVENTOR(S) | : McKay | |

It is certified that error appears in the above-identified patent and that said Letters Patent is hereby corrected as shown below:

On the Title Page

In Item (56), under "U.S. PATENT DOCUMENTS", in Column 2, Line 1, delete "Bruneau" and insert -- Bruneau et al. --, therefor.

In Item (56), under "U.S. PATENT DOCUMENTS", in Column 2, Line 4, delete "Biedermann" and insert -- Biedermann et al. --, therefor.

In Item (56), under "U.S. PATENT DOCUMENTS", in Column 2, Line 6, delete "Serhan" and insert -- Serhan et al. --, therefor.

In Item (56), under "U.S. PATENT DOCUMENTS", in Column 2, Line 9, delete "Bhatnagar" and insert -- Bhatnagar et al. --, therefor.

In the Specification

In Column 8, Line 27, delete "mating parts 28, 30" and insert -- mating parts 30, 32 --, therefor.

In Column 8, Line 60, delete "spacer 20" and insert -- spacer 10 --, therefor.

In Column 9, Lines 44-45, delete "sulfasalazine[2-hydroxy-5-[-4-[C2-pyridinylamino)sulfonyl]azo]benzoic acid]," and insert -- sulfasalazine [2-hydroxy-5-[[4-[(2-pyridinylamino)sulfonyl]phenyl]azo]benzoic acid], --, therefor.

Signed and Sealed this
Seventeenth Day of October, 2017

Joseph Matal
*Performing the Functions and Duties of the*
*Under Secretary of Commerce for Intellectual Property and*
*Director of the United States Patent and Trademark Office*